United States Patent
Kuo et al.

(10) Patent No.: US 11,655,509 B2
(45) Date of Patent: May 23, 2023

(54) KITS FOR DIAGNOSING SPINAL MUSCULAR ATROPHY AND USES THEREOF

(71) Applicant: Origin Biotechnology Co., Ltd., Taipei (TW)

(72) Inventors: Yi-Yi Kuo, New Taipei (TW); I-Fan Chiu, Hsinchu (TW); Lai-Ha Chung, New Taipei (TW); Shu-Ju Lee, New Taipei (TW)

(73) Assignee: Origin Biotechnology Co., Ltd., Taipei (TW)

( * ) Notice: Subject to any disclaimer, the term of this patent is extended or adjusted under 35 U.S.C. 154(b) by 133 days.

(21) Appl. No.: 17/151,225

(22) Filed: Jan. 18, 2021

(65) Prior Publication Data

US 2021/0277473 A1    Sep. 9, 2021

(30) Foreign Application Priority Data

Mar. 3, 2020 (CN) .......................... 202010138478.6

(51) Int. Cl.
*C12Q 1/6883* (2018.01)

(52) U.S. Cl.
CPC ...... *C12Q 1/6883* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

FOREIGN PATENT DOCUMENTS

| CN | 104630368 A | * | 5/2015 |
| WO | WO 2014/210199 | * | 12/2014 |

OTHER PUBLICATIONS

NCBI Database, NCBI reference sequence NG_000006.1, Nov. 1, 2019, available via URL: < ncbi.nlm.nih.gov/nuccore/NG_000006.1?from=33739&to=34573&report=genbank> (Year: 2019).*

* cited by examiner

*Primary Examiner* — Carla J Myers (57) ABSTRACT

Disclosed herein is a kit for diagnosing spinal muscular atrophy (SMA) in a human subject based on the copy numbers of exons 7 and 8 of SMN1 gene and the copy numbers of exons 7 and 8 of SMN2 gene in a DNA sample isolated from the human subject. Also disclosed herein are methods of diagnosing SMA by use of the present kit, and methods of treating SMA based on the diagnostic result.

4 Claims, 3 Drawing Sheets

Specification includes a Sequence Listing.

SEQUENCE LISTING

<160> NUMBER OF SEQ ID NOS: 18

<210> SEQ ID NO 1
<211> LENGTH: 26
<212> TYPE: DNA
<213> ORGANISM: Artificial Sequence
<220> FEATURE:
<223> OTHER INFORMATION: synthesized_the first polynucleotide sequence

<400> SEQUENCE: 1
gcagcctaat aattgttttc tttggg                                    26

<210> SEQ ID NO 2
<211> LENGTH: 25
<212> TYPE: DNA
<213> ORGANISM: Artificial Sequence
<220> FEATURE:
<223> OTHER INFORMATION: synthesized_the second polynucleotide sequence
<220> FEATURE:
<221> NAME/KEY: variation
<222> LOCATION: 23,24
<223> OTHER INFORMATION: /note="n is A, T, C, or G"

<400> SEQUENCE: 2
ccttccttct ttttgatttt gtnng                                     25

<210> SEQ ID NO 3
<211> LENGTH: 26
<212> TYPE: DNA
<213> ORGANISM: Artificial Sequence
<220> FEATURE:
<223> OTHER INFORMATION: synthesized_the third polynucleotide sequence
<220> FEATURE:
<221> NAME/KEY: variation
<222> LOCATION: 24,25
<223> OTHER INFORMATION: /note="n is A, T, C, or G"

<400> SEQUENCE: 3
accttccttc tttttgattt tgtnna                                    26

<210> SEQ ID NO 4
<211> LENGTH: 23
<212> TYPE: DNA
<213> ORGANISM: Artificial Sequence
<220> FEATURE:
<223> OTHER INFORMATION: synthesized_the fourth polynucleotide sequence

<400> SEQUENCE: 4
agccatgtcc accagttaga ttc                                       23

<210> SEQ ID NO 5
<211> LENGTH: 21
<212> TYPE: DNA
<213> ORGANISM: Artificial Sequence
<220> FEATURE:
<223> OTHER INFORMATION: synthesized_the fifth polynucleotide sequence
<220> FEATURE:
<221> NAME/KEY: variation
<222> LOCATION: 19,20
<223> OTHER INFORMATION: /note="n is A, T, C, or G"

<400> SEQUENCE: 5
aaaccatctg taaaagacnn g                                         21

<210> SEQ ID NO 6
<211> LENGTH: 21
<212> TYPE: DNA
<213> ORGANISM: Artificial Sequence
<220> FEATURE:
<223> OTHER INFORMATION: synthesized_the sixth polynucleotide sequence
<220> FEATURE:
<221> NAME/KEY: variation
<222> LOCATION: 19,20
<223> OTHER INFORMATION: /note="n is A, T, C, or G"

<400> SEQUENCE: 6
aaaccatctg taaaagacnn a                                         21

<210> SEQ ID NO 7
<211> LENGTH: 21
<212> TYPE: DNA
<213> ORGANISM: Artificial Sequence
<220> FEATURE:
<223> OTHER INFORMATION: synthesized_the seventh primer

<400> SEQUENCE: 7
tcgacgcacg ctcctgctac a                                         21

<210> SEQ ID NO 8
<211> LENGTH: 20
<212> TYPE: DNA
<213> ORGANISM: Artificial Sequence
<220> FEATURE:
<223> OTHER INFORMATION: synthesized_the eighth primer

<400> SEQUENCE: 8
tgaccgtctg cgcctcgttc                                           20

<210> SEQ ID NO 9
<211> LENGTH: 45
<212> TYPE: DNA
<213> ORGANISM: Artificial Sequence
<220> FEATURE:

<223> OTHER INFORMATION: synthesized_the first primer

<400> SEQUENCE: 9
tcgacgcacg ctcctgctac agcagcctaa taattgtttt ctttg    45

<210> SEQ ID NO 10
<211> LENGTH: 45
<212> TYPE: DNA
<213> ORGANISM: Artificial Sequence
<220> FEATURE:
<223> OTHER INFORMATION: synthsized_the second primer

<400> SEQUENCE: 10
tgaccgtctg cgcctcgttc ccttccttct ttttgatttt gtcgg    45

<210> SEQ ID NO 11
<211> LENGTH: 51
<212> TYPE: DNA
<213> ORGANISM: Artificial Sequence
<220> FEATURE:
<223> OTHER INFORMATION: synthsized_the third primer

<400> SEQUENCE: 11
tgaccgtctg cgcctcgttc acttcacctt ccttctttt gattttgtat a    51

<210> SEQ ID NO 12
<211> LENGTH: 44
<212> TYPE: DNA
<213> ORGANISM: Artificial Sequence
<220> FEATURE:
<223> OTHER INFORMATION: synthsized_the fourth primer

<400> SEQUENCE: 12
tcgacgcacg ctcctgctac aagccatgtc caccagttag attc    44

<210> SEQ ID NO 13
<211> LENGTH: 41
<212> TYPE: DNA
<213> ORGANISM: Artificial Sequence
<220> FEATURE:
<223> OTHER INFORMATION: synthsized_the fifth primer

<400> SEQUENCE: 13
tgaccgtctg cgcctcgttc aaaccatctg taaaagaccg g    41

<210> SEQ ID NO 14
<211> LENGTH: 46
<212> TYPE: DNA
<213> ORGANISM: Artificial Sequence
<220> FEATURE:
<223> OTHER INFORMATION: synthsized_the sixth primer

<400> SEQUENCE: 14
tgaccgtctg cgcctcgttc acttcaaacc atctgtaaaa gacgga    46

<210> SEQ ID NO 15
<211> LENGTH: 41
<212> TYPE: DNA
<213> ORGANISM: Artificial Sequence
<220> FEATURE:
<223> OTHER INFORMATION: synthesized_ the forward primer of beta-actin

<400> SEQUENCE: 15
tgaccgtctg cgcctcgttc catgtacgtt gctatccagg c    41

```
<210> SEQ ID NO 16
<211> LENGTH: 43
<212> TYPE: DNA
<213> ORGANISM: Artificial Sequence
<220> FEATURE:
<223> OTHER INFORMATION: synthesized_ the reverse primer of beta-actin

<400> SEQUENCE: 16
tcgacgcacg ctcctgctac agctcattgc caatggtgat gac          43

<210> SEQ ID NO 17
<211> LENGTH: 40
<212> TYPE: DNA
<213> ORGANISM: Artificial Sequence
<220> FEATURE:
<223> OTHER INFORMATION: synthesized_the forward primer of HBB

<400> SEQUENCE: 17
tgaccgtctg cgcctcgttc acacaactgt gttcactagc              40

<210> SEQ ID NO 18
<211> LENGTH: 43
<212> TYPE: DNA
<213> ORGANISM: Artificial Sequence
<220> FEATURE:
<223> OTHER INFORMATION: synthesized_the reverse primer of HBB

<400> SEQUENCE: 18
tcgacgcacg ctcctgctac atggtctcct taaacctgtc ttg          43
```

KITS FOR DIAGNOSING SPINAL MUSCULAR ATROPHY AND USES THEREOF

CROSS-REFERENCE TO RELATED APPLICATIONS

This application relates to and claims the benefit of China Application No. 202010138478.6, filed Mar. 3, 2020; the content of the application is incorporated herein by reference in its entirety.

BACKGROUND OF THE INVENTION

1. Field of the Invention

The present disclosure in general relates to the field of disease diagnosis. More particularly, the present disclosure relates to a kit comprising eight primers with specific polynucleotide sequences, and uses of the kit in the diagnosis of spinal muscular atrophy (SMA).

2. Description of Related Art

Spinal muscular atrophy (SMA) is a genetic disorder characterized by the loss of motor neurons and progressive muscle wasting. It is one of the most prevalent genetic disorders affecting young children and a major cause of death in infancy. There are four types of SMA starting at different ages, including, (1) SMA type 1, also known as Werdnig-Hoffmann disease, which is the most severe form developing in babies less than 6 months old; affected babies usually have feeding difficulties, and die from respiratory failure or aspiration before the age of 2 years; (2) SMA type 2, which appears in babies at about 6 to 18 months old; affected patients usually have hypotonia, delayed motor milestones, and are able to sit unsupported, but cannot stand or walk unaided; the life expectancy of the affected patients depends on the degree of respiratory muscle involvement but is usually greater than 4 years; (3) SMA type 3, also known as Kugelberg-Welander disease, which develops after 18 months of age; affected patients are able to walk unaided, but would fall frequently and have a shuffling gait, foot drop and difficulty with stairs; the life expectancy of SMA type 3 patients is normal or near normal, and most patients require mobility supports; and (4) SMA type 4, which affects adults and usually only causes mild problems, such as muscle weakness in upper arms and leg muscles with minor breathing problems. The incidence of SMA is about 1 in 10,000 live births, and the carrier frequency is about 1 in 50 people. Typical symptoms of SMA include, floppy or weak arms and legs, movement problem (e.g., having difficulty in sitting, crawling, and/or walking), twitching or shaking muscles, bond and join problems (e.g., an unusually curved spine), swallowing problems, and breathing problems (e.g., respiratory distress).

SMA is caused by a mutation in Survival of motor neuron 1 (SMN1) gene, which encodes SMN1, a protein necessary for the survival and function of motor neurons. Loss of these motor neurons in the spinal cord blocks the signal transduction between the brain and skeletal muscles. SMN2, a gene 875 Kb away from SMN1 gene, is regarded as a disease modifying gene that compensates for the loss of SMN1 gene in a dose-dependent manner. The full-length nucleotide sequences of the two genes are identical except for two nucleotide substitutions respectively located in exons 7 and 8. The nucleotide C in the exon 7 of SMN1 gene ensures that the exon 7 is included in the final mature SMN1 mRNA. By contrast, a C to T base change in the exon 7 of SMN2 gene causes substantial skipping of this exon that results in the low levels of functional protein. Aside from the base change occurred in exon 7, the SMN2 gene can alternatively be distinguished from the SMN1 gene by a G to A base change in exon 8 that creates a Dde I site. After gene amplification and enzyme treatment, the SMN1 protein would be presented in an undigested from (about 200 bp), while the SMN2 protein would be digested into 122 bp and 78 bp products. In a normal individual who have both SMN1 and SMN2 genes, the SMN1 gene contributes 90% of SMN protein, while the SMN2 gene only contributes 10% of SMN protein. An individual with only SMN2 gene usually cannot produce sufficient amount of SMN protein, and therefore is affected by SMA.

Molecular genetic testing is the standard tool for diagnosis of SMA. Polymerase chain reaction-restriction fragment length polymorphism (PCR-RFLP) is a traditional method for molecular characterization of SMA, but its precision is compromised due to incomplete digestion. Allele-specific (AS)-PCR, also known as amplification refractory mutation system (ARMS), differentiates single base changes by PCR assay thereby addressing the incomplete digestion issue of PCR-RFLP; however, about 5% of patients have point mutations instead of gross deletion of SMN1 gene, and AS-PCR fails to detect these point mutations. Multiplex ligation-dependent probe amplification (MLPA) and quantitative real-time PCR (RT-PCR) provide alternatively methods for diagnosing SMA via detecting the copy number of specific genomic loci. Nonetheless, MLPA is extremely sensitive to impurities, and is not able to detect structural chromosome aberrations and mosaicism. Regarding RT-PCR, its accuracy would be affected by DNA extraction methods and template quantification. High-resolution melting analysis (HRMA) is a new technology for SMA detection, but its accuracy and specificity need to be improved, and the positive results still require sequencing for diagnostic confirmation. Denaturing high performance liquid chromatography (DHPLC) is a costly and time consuming procedure that requires mixing samples with control homozygous wild-type DNA for the purpose of identifying homozygous and hemizygous mutations.

In view of the foregoing, there exists in the related art a need for an improved method for detecting the mutations of SMN1 and SMN2 genes in a subject in a more accurate and specific manner so as to determine whether such the subject has SMA or is a carrier of SMA.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a kit for making a diagnosis as to whether a human subject has spinal muscular atrophy (SMA) or is a carrier of SMA. According to some embodiments of the present disclosure, the kit comprises eight primers and polymerase chain reaction (PCR) reagents, in which the first primer comprises a first polynucleotide sequence of SEQ ID NO: 1, and a first non-human sequence disposed at and connected to the 5'-end of the first polynucleotide sequence;

the second primer comprises a second polynucleotide sequence of SEQ ID NO: 2, and a second non-human sequence disposed at the 5'-end of the second polynucleotide sequence;

the third primer comprises a third polynucleotide sequence of SEQ ID NO: 3, and the second non-human sequence disposed at the 5'-end of the third polynucleotide sequence;

the fourth primer comprises a fourth polynucleotide sequence of SEQ ID NO: 4, and the first non-human sequence disposed at and connected to the 5'-end of the fourth polynucleotide sequence;

the fifth primer comprises a fifth polynucleotide sequence of SEQ ID NO: 5, and the second non-human sequence disposed at the 5'-end of the fifth polynucleotide sequence;

the sixth primer comprises a sixth polynucleotide sequence of SEQ ID NO: 6, and the second non-human sequence disposed at the 5'-end of the sixth polynucleotide sequence;

the seventh primer consists of the first non-human sequence; and the eighth primer consists of the second non-human sequence.

Optionally, the second primer or the third primer further comprises a third non-human sequence. According to certain embodiments, the third non-human sequence is present in the second primer; in these embodiments, the third non-human sequence is disposed between the second non-human sequence and the second polynucleotide sequence. According to alternative embodiments, the third non-human sequence is present in the third primer; in these embodiments, the third non-human sequence is disposed between the second non-human sequence and the third polynucleotide sequence.

Additionally or alternatively, the fifth or the sixth primers further comprises a third non-human sequence. In some embodiments, the third non-human sequence is present in the fifth primer, and is disposed between the second non-human sequence and the fifth polynucleotide sequence. In certain embodiments, the third non-human sequence is present in the sixth primer, and is disposed between the second non-human sequence and the sixth polynucleotide sequence.

According to some working examples of the present disclosure, the first non-human sequence has the polynucleotide sequence of SEQ ID NO: 7; the second non-human sequence has the polynucleotide sequence of SEQ ID NO: 8; and the third non-human sequence comprises the polynucleotide sequence of "ACTTC".

In one specific example, the first primer has the polynucleotide sequence of SEQ ID NO: 9; the second primer has the polynucleotide sequence of SEQ ID NO: 10; the third primer has the polynucleotide sequence of SEQ ID NO: 11; the fourth primer has the polynucleotide sequence of SEQ ID NO: 12; the fifth primer has the polynucleotide sequence of SEQ ID NO: 13; the sixth primer has the polynucleotide sequence of SEQ ID NO: 14; the seventh primer has the polynucleotide sequence of SEQ ID NO: 7; and the eighth primer has the polynucleotide sequence of SEQ ID NO: 8.

Optionally, the eighth primer is conjugated with a reporter molecule.

Optionally, the present kit further comprises two DNA templates as internal controls, in which the first DNA template has two copy numbers of beta-actin ((3-actin) gene within the polynucleotide sequence thereof; and the second DNA template has two copy numbers of haemoglobin beta (HBB) gene within the polynucleotide sequence thereof.

The PCR reagents of the present kit optionally comprise DNA polymerase, buffer, $MgCl_2$, deoxynucleotide triphosphates (dNTPs), and betaine.

The second aspect of the present disclosure is directed to a method of making a diagnosis as to whether a human subject has SMA or is a carrier of SMA by using the kit according to any embodiment or example of the present disclosure. The method comprises, (a) extracting a DNA sample from the human subject;

(b) mixing the DNA sample with the first to eighth primers in the PCR reagents;

(c) subjecting the mixture of the step (b) to PCR;

(d) determining a first copy number of exon 7 of SMN1 gene, a second copy number of exon 7 of SMN2 gene, a third copy number of exon 8 of SMN1 gene, and a fourth copy number of exon 8 of SMN2 gene in the DNA sample from the product of the step (c); wherein when the sum of the first and the second copy numbers is not equal to the sum of the third and fourth copy numbers, then repeating steps (b) and (c) until the sum of the first and the second copy numbers equals to the sum of the third and fourth copy numbers; and (e) making the diagnosis of SMA based on the first copy number determined by the step (d), wherein when the first copy number is 0, then diagnosing the human subject has the SMA; or when the first copy number is 1, then diagnosing the human subject is the carrier of the SMA.

Based on the diagnostic result, a clinical practitioner or a skilled artisan may administer to an SMA patient a suitable treatment in time. Accordingly, also disclosed herein is a method of treating SMA in a subject. The method comprises, (a) extracting a DNA sample from the human subject;

(b) mixing the DNA sample with the first to eighth primers in the PCR reagents;

(c) subjecting the mixture of the step (b) to PCR;

(d) determining a first copy number of exon 7 of SMN1 gene, a second copy number of exon 7 of SMN2 gene, a third copy number of exon 8 of SMN1 gene, and a fourth copy number of exon 8 of SMN2 gene in the DNA sample from the product of the step (c); wherein when the sum of the first and the second copy numbers is not equal to the sum of the third and fourth copy numbers, then repeating steps (b) and (c) until the sum of the first and the second copy numbers equals to the sum of the third and fourth copy numbers; and (e) treating the SMA based on the first copy number determined by the step (d), wherein when the first copy number is 0, administering to the human subject an effective amount of a therapeutic agent.

Depending on desired purposes, the SMA treatment may be nusinersen, risdiplam, onasemnogene abeparvovec, or a combination thereof.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. DEFINITION

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "polynucleotide sequence" is understood to mean either a double-stranded DNA or a single-stranded DNA. The polynucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

The term "copy number" as used herein refers to the number of a polynucleotide sequence (e.g., exon 7 of SMN1 gene, exon 8 of SMN1 gene, exon 7 of SMN2 gene, or exon 8 of SMN2 gene) in the genome of a subject, e.g., a human. According to the present disclosure, the copy number of exon 7 of SMN1 gene means the number of exon 7 of SMN1 gene on chromosome 5 of a subject; the copy number of exon 8 of SMN1 gene means the number of exon 8 of SMN1 gene on chromosome 5 of a subject; the copy number of exon 7 of SMN2 gene means the number of exon 7 of SMN2 gene on chromosome 5 of a subject; and the copy number of exon 8 of SMN2 gene means the number of exon 8 of SMN2 gene on chromosome 5 of a subject. Copy number may be determined from one single cell, or be determined from a group of cells (e.g., tissue sample). When comparing the "copy number" in the genome of a subject, one need not determine the exact copy number of the subject, but instead need only obtain an approximation that allows one to determine whether a given subject contains more or less of the polynucleotide sequence as compared to another subject. Methods for determining the copy number of a polynucleotide sequence are well-known in the art, for example, Southern analysis, quantitative PCR, real time PCR, and DNA sequencing.

The term "diagnosis" as used herein refers to methods by which a skilled artisan can estimate and/or determine the probability ("a likelihood") of whether or not a patient is suffering from a given disease or condition. In the case of the present invention, "diagnosis" includes using the PCR product amplified by the four primers of the present kit, optionally together with other clinical characteristics, to arrive at a diagnosis (that is, the occurrence or nonoccurrence) of SMA for the subject from which a DNA sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

As used herein, the term "non-human" refers to any animal other than the human species, from whom a sequence (i.e., the first, second, and third non-human sequences of the present disclosure) is obtained (i.e., directly cloning from the non-human animal without any modification) or derived (i.e., cloning from the non-human animal with one or more modifications; such as, replacement or deletion of one or more nucleic acids of the sequence). The non-human animals suitable for obtaining or deriving the present non-human sequence include, but are not limited to, mouse, rat, hamster, guinea pig, rabbit, pig, monkey, sheep, goat, horse, cat, dog, chimpanzee, ape, orangutan, wolf, deer, donkey, zebra, bear, giraffe, lion, and tiger. According to some embodiments of the present disclosure, the non-human sequence of the present kit is derived from bacteriophage without sequence modification.

As used herein, the term "PCR reagents" refers to the chemicals, apart from the specified primers (i.e., the first to the eighth primers of the present kit), needed to perform the PCR process. These chemicals generally comprise four classes of components: (i) an aqueous buffer (also known as PCR buffer), (ii) a water soluble magnesium salt (e.g., $MgCl_2$), (iii) at least four deoxyribonucleotide triphosphates (dNTPs, including thymidine triphosphate (dTTP), deoxyadenosine triphosphate (dATP), deoxycitidine triphosphate (dCTP) and deoxyguanosine triphosphate (dGTP)), and (iv) a polynucleotide polymerase, preferably a DNA polymerase, more preferably a thermostable DNA polymerase, i.e., a DNA polymerase, which can tolerate temperatures between 90° C. and 100° C. for a total time of at least 10 minutes without losing more than about half its activity. Depending on desired purposes, these chemicals may comprise one or more additional components for improving the efficacy and/or specificity of the PCR process, such as betaine, ethylene glycol, and/or glycerol.

The term "subject" refers to a human species diagnosed by the kit and/or method of the present invention. The term "subject" is intended to refer to both the male and female gender unless one gender is specifically indicated.

II. DESCRIPTION OF THE INVENTION

The present disclosure aims at providing a method of performing PCR to determine the copy numbers of exon 7 of SMN1 gene, exon 8 of SMN1 gene, exon 7 of SMN2 gene, or exon 8 of SMN2 gene in a biological sample by use of a first to an eighth primers. Also disclosed herein are a kit and a method for diagnosing whether a human subject has SMA, or is a carrier of SMA based on the determined copy numbers, so that a clinical practitioner or a skilled artisan may administer to an SMA patient a suitable treatment in time, and providing a genetic counseling to an SMA carrier with risk assessment thereby reducing or preventing maternal transmission.

(II-1) Kits for Diagnosing SMA

The first aspect of the present disclosure pertains to a kit for diagnosing SMA. According to embodiments of the present disclosure, the kit comprises eight primers and polymerase chain reaction (PCR) reagents.

Figure 1:
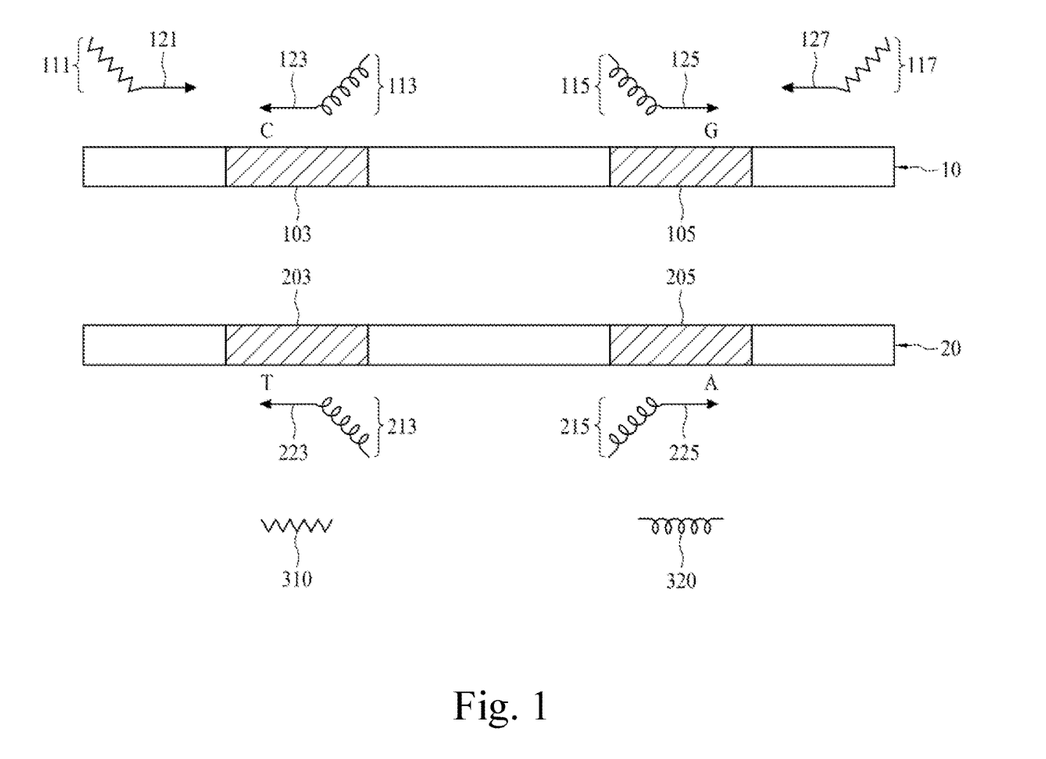
FIG. 1 is a schematic diagram depicting the design of the preset primers.

Reference is made to FIG. 1, which depicts the primer design of the present disclosure. The SMN1 gene (10) comprises exon 7 (103) and exon 8 (105), and the SMN2 gene (20) comprises exon 7 (203) and exon 8 (205). As mentioned above, the nucleotide sequences of the two genes are identical except for two nucleotide substitutions respectively located in exons 7 and 8, in which the nucleotide "C" in the exon 7 (103) of the SMN1 gene (10) is changed to be the nucleotide "T" in the exon 7 (203) of the SMN2 gene (20), and the nucleotide "G" in the exon 8 (105) of the SMN1 gene (10) is changed to be the nucleotide "A" in the exon 8 (205) of the SMN2 gene (20).

According to FIG. 1, the first primer (111) comprises a first polynucleotide sequence (121) and a non-human sequence (310) disposed at the 5'-end of the first polynucleotide sequence (121), wherein the first polynucleotide sequence (121) is complementary to the upstream sequence of the exon 7 (103, 203). The second primer (113) comprises a second polynucleotide sequence (123) and a second non-human sequence (320) disposed at the 5'-end of the second polynucleotide sequence (123), wherein the second polynucleotide sequence (123) is complementary to the sequence of exon 7 (103). The third primer (213) comprises a third polynucleotide sequence (223) and the second non-human sequence (320) disposed at the 5'-end of the third polynucleotide sequence (223), wherein the third polynucleotide sequence (223) is complementary to the sequence of exon 7 (203). The fourth primer (117) comprises a fourth polynucleotide sequence (127) and the first non-human sequence (310) disposed at the 5'-end of the fourth polynucleotide sequence (127), wherein the fourth polynucleotide sequence (127) is complementary to the downstream sequence of exon 8 (105, 205). The fifth primer (115) comprises a fifth polynucleotide sequence (125) and the second non-human sequence (320) disposed at the 5'-end of the fifth polynucleotide sequence (125), wherein the fifth polynucleotide sequence (125) is complementary to the sequence of exon 8 (105). The sixth primer (215) comprises a sixth polynucleotide sequence (225) and the second non-human sequence (320) disposed at the 5'-end of the sixth polynucleotide sequence (225), wherein the sixth polynucleotide sequence (225) is complementary to the sequence of exon 8 (205). The seventh primer consists of the first non-human sequence (310). The eighth primer consists of the second non-human sequence (320).

According to some embodiments of the present disclosure, the first polynucleotide sequence (121) has the polynucleotide sequence of "GCAGCCTAATAATTGTTTTCTTTGGG" (SEQ ID NO: 1); the second polynucleotide sequence (123) has the polynucleotide sequence of "CCTTCCTTCTTTTTGATTTTGTNNG" (SEQ ID NO: 2); the third polynucleotide sequence (223) has the polynucleotide sequence of "ACCTTCCTTCTTTTTGATTTTGTNNA" (SEQ ID NO: 3); the fourth polynucleotide sequence (127) has the polynucleotide sequence of "AGCCATGTCCACCAGTTAGATTC" (SEQ ID NO: 4); the fifth polynucleotide sequence (125) has the polynucleotide sequence of "AAACCATCTGTAAAAGACNNG" (SEQ ID NO: 5); the sixth polynucleotide sequence (225) has the polynucleotide sequence of "AAACCATCTGTAAAAGACNNA" (SEQ ID NO: 6).

Two "N" nucleotides are present in each of SEQ ID NOs: 2, 3, 5, and 6. According to the symbols set forth in WIPO Standard ST.25 (1998), N represents any of A, T, C or G nucleotide. A skilled artisan may adjust the type of the "N" nucleotide (i.e., selecting A, T, C or G as the N nucleotide)

in the polynucleotide sequences of SEQ ID NOs: 2 and 3 in accordance with desired purposes to distinguish the amplified exon 7 fragment of SMN1 gene and the amplified exon 7 fragment of SMN2 gene thereby improving the diagnostic specificity. Similarly, the "N" nucleotide in the polynucleotide sequences of SEQ ID NOs: 5 and 6 can be adjusted in accordance with desired purposes thereby distinguishing the amplified exon 8 fragment of SMN1 gene and the amplified exon 8 fragment of SMN2 gene for the purpose of improving the diagnostic specificity.

According to some preferred embodiments, the nucleotides at positions 23 and 24 of SEQ ID NO: 2 (i.e., the first and second "N" nucleotides of SEQ ID NO: 2, from 5'-end to 3'-end) are respectively "C" and "G"; i.e., the second polynucleotide sequence has the nucleotide sequence of "GTCGG" at its 3'-end;

the nucleotides at positions 24 and 25 of SEQ ID NO: 3 (i.e., the first and second "N" nucleotides of SEQ ID NO: 3, from 5'-end to 3'-end) are respectively "A" and "T"; i.e., the third polynucleotide sequence has the nucleotide sequence of "GTATA" at its 3'-end;

the nucleotides at positions 19 and 20 of SEQ ID NO: 5 (i.e., the first and second "N" nucleotides of SEQ ID NO: 5, from 5'-end to 3'-end) are respectively "C" and "G"; i.e., the fifth polynucleotide sequence has the nucleotide sequence of "ACCGG" at its 3'-end; and the nucleotides at positions 19 and 20 of SEQ ID NO: 6 (i.e., the first and second "N" nucleotides of SEQ ID NO: 6, from 5'-end to 3'-end) are respectively "G" and "G"; i.e., the sixth polynucleotide sequence has the nucleotide sequence of "ACGGA" at its 3'-end.

According to certain embodiment, the second, third, fifth and sixth polynucleotide sequences respectively have the nucleotide sequences of "GTCGG", "GTATA", "ACCGG" and "ACTCA" at the 3'-end thereof. According to certain embodiment, the second, third, fifth and sixth polynucleotide sequences respectively have the nucleotide sequences of "GTCCG", "GTGTA", "ACCGG" and "ACTCA" at the 3'-end thereof. According to certain embodiment, the second, third, fifth and sixth polynucleotide sequences respectively have the nucleotide sequences of "GTCAG", "GTGTA", "ACAGG" and "ACTCA" at the 3'-end thereof. According to certain embodiment, the second, third, fifth and sixth polynucleotide sequences respectively have the nucleotide sequences of "GTATG", "GTCCA", "ACCGG" and "ACGGA" at the 3'-end thereof. According to certain embodiment, the second, third, fifth and sixth polynucleotide sequences respectively have the nucleotide sequences of "GTATG", "GTCCA", "ACCGG" and "ACTCA" at the 3'-end thereof. According to certain embodiment, the second, third, fifth and sixth polynucleotide sequences respectively have the nucleotide sequences of "GTATG", "GTCGA", "ACCGG" and "ACTCA" at the 3'-end thereof. According to certain embodiment, the second, third, fifth and sixth polynucleotide sequences respectively have the nucleotide sequences of "GTTTG", "GTCGA", "ACCGG" and "ACTCA" at the 3'-end thereof. According to certain embodiment, the second, third, fifth and sixth polynucleotide sequences respectively have the nucleotide sequences of "GTCGG", "GTCCA", "ACCGG" and "ACGGA" at the 3'-end thereof. According to certain embodiment, the second, third, fifth and sixth polynucleotide sequences respectively have the nucleotide sequences of "GTCGG", "GTGTA", "ACGGG" and "ACTCA" at the 3'-end thereof. According to certain embodiment, the second, third, fifth and sixth polynucleotide sequences respectively have the nucleotide sequences of "GTCCG", "GTGTA", "ACTAG" and "ACGGA" at the 3'-end thereof. According to certain embodiment, the second, third, fifth and sixth polynucleotide sequences respectively have the nucleotide sequences of "GTATG", "GTCCA", "ACTCG" and "ACCGA" at the 3'-end thereof.

According to some working examples, the first non-human sequence (310) and the second non-human sequence (320) respectively have the polynucleotide sequences of SEQ ID NOs: 7 and 8.

In practice, the first and the second primers (111, 113) respectively serve as the forward and reverse primers for amplifying the sequence of exon 7 (103) of SMN1 gene (10), and the first and the third primers (111, 213) respectively serve as the forward and reverse primers for amplifying the sequence of exon 7 (203) of SMN2 gene (20). The thus-obtained exon 7 segments (i.e., the DNA segments of exon 7 (103, 203) respectively amplified by the first and the second primers (111, 113) and the first and the third primers (111, 213)) comprises the first non-human sequence (310) at the 5'end thereof, and the second non-human sequence (320) at the 3'end thereof. In this way, the exon 7 segments may further be amplified by the seventh and eighth primers (310, 320).

Similarly, the fifth and fourth primers (115, 117) respectively serve as the forward and reverse primers for amplifying the sequence of exon 8 (105) of SMN1 gene (10), and the sixth and fourth primers (215, 117) respectively serve as the forward and reverse primers for amplifying the sequence of exon 8 (205) of SMN2 gene (20). The thus-obtained exon 8 segments (i.e., the DNA segments of exon 8 (105, 205) respectively amplified by the fifth and fourth primers (115, 117) and the sixth and fourth primers (215, 117)) comprises the second non-human sequence (320) at the 5'-end thereof, and the first non-human sequence (310) at the 3'-end thereof. In this way, the exon 8 segments may further be amplified by the seventh and eighth primers (310, 320).

A skilled artisan may decide the copy numbers of exons 7 and 8 of SMN1 gene and exons 7 and 8 of SMN2 gene by subjecting the exon 7 and exon 8 segments to an electrophoresis assay (e.g., a capillary electrophoresis assay), and comparing the peak areas of the DNA fragments to that of a control sample derived from a healthy subject. Based on the analytic results, a skilled artisan may determine the copy numbers of specific exon sequences (i.e., exons 7 and 8) of SMN1 and SMN2 genes, thereby making a diagnosis of SMA or the severity of SMA. According to some embodiments of the present disclosure, when the copy number of exon 7 of SMN1 gene is 0, then the subject is diagnosed as having SMA; alternatively, when the copy number of exon 7 of SMN1 gene is 1, then the subject is diagnosed as being a carrier of SMA. According to certain embodiments, the severity of SMA is determined from the copy numbers of exon 8 of SMN1 gene and exons 7 and 8 of SMN2 gene, which are inversely proportional to the severity of SMA.

Optionally, the second primer or the third primer further comprises a third non-human sequence so as to distinguish the exon 7 segments of SMN1 and SMN2 genes. According to some embodiments, the third non-human sequence is present in the second primer, and is disposed between the second non-human sequence and the second polynucleotide sequence. According to alternative embodiments, the third non-human sequence is present in the third primer, and is disposed between the second non-human sequence and the third polynucleotide sequence.

Additionally or alternatively, the fifth or the sixth primers further comprises a third non-human sequence so as to distinguish the exon 8 segments of SMN1 and SMN2 genes.

According to some embodiments, the third non-human sequence is present in the fifth primer, and is disposed between the second non-human sequence and the fifth polynucleotide sequence. According to alternative embodiments, the third non-human sequence is present in the sixth primer, and is disposed between the second non-human sequence and the sixth polynucleotide sequence.

According to some working examples of the present disclosure, the first non-human sequence has the polynucleotide sequence of SEQ ID NO: 7; the second non-human sequence has the polynucleotide sequence of SEQ ID NO: 8; and the third non-human sequence comprises the polynucleotide sequence of "ACTTC".

In one specific example, the first primer has the polynucleotide sequence of SEQ ID NO: 9; the second primer has the polynucleotide sequence of SEQ ID NO: 10; the third primer has the polynucleotide sequence of SEQ ID NO: 11; the fourth primer has the polynucleotide sequence of SEQ ID NO: 12; the fifth primer has the polynucleotide sequence of SEQ ID NO: 13; the sixth primer has the polynucleotide sequence of SEQ ID NO: 14; the seventh primer has the polynucleotide sequence of SEQ ID NO: 7; and the eighth primer has the polynucleotide sequence of SEQ ID NO: 8.

Optionally, the 3'- or 5'-end of the eighth primer is conjugated with a reporter molecule. Non-limiting examples of reporter molecule suitable to be conjugated with the eighth primer include, but are not limited to, a fluorescent molecule, a luminescent molecule, a phosphorescent molecule, a colorimetric dye, a contrast agent, and an enzyme.

According to optional embodiments of the present disclosure, the present kit further comprises two DNA templates as internal controls, in which the first DNA template has two copy numbers of beta-actin (β-actin) gene within the polynucleotide sequence thereof; and the second DNA template has two copy numbers of haemoglobin beta (HBB) gene within the polynucleotide sequence thereof. After conducting the PCR process with the eight primers of the present kit and analyzing by a detection technique (e.g., a capillary electrophoresis assay), four peak areas, respectively corresponding to the PCR products of exon 7 of SMN1 gene, exon 8 of SMN1 gene, exon 7 of SMN2 gene and exon 8 of SMN2 gene, are obtained; each peak area is then normalized with the peak areas of internal controls thereby determining the copy numbers of desired exon sequences.

According to embodiments of the present disclosure, in addition to the eight primers described above, the present kit further comprises PCR reagents for amplifying DNA segments in PCR assay. In certain examples, the PCR reagents comprise DNA polymerase, PCR buffer (e.g., Tris(hydroxymethyl)aminomethane buffer (Tris buffer), Tris-HCl buffer, or any aqueous buffer known by skilled artisan for conducting the PCR process), $MgCl_2$, deoxynucleotide triphosphates (dNTPs, including dATP, dTTP, dGTP, and dCTP), and betaine.

(II-2) Methods for Diagnosing SMA

Also disclosed herein is a method for making a diagnosis as to whether a human subject has SMA or is a carrier of SMA by using the kit in accordance with any embodiment or example of the present disclosure. The present method comprises the steps of, (a) extracting a DNA sample from the human subject;
(b) mixing the DNA sample with the first to eighth primers in the PCR reagents;
(c) subjecting the mixture of the step (b) to PCR;

(d) determining a first copy number of exon 7 of survival of motor neuron 1 (SMN1) gene, a second copy number of exon 7 of survival of motor neuron 2 (SMN2) gene, a third copy number of exon 8 of the SMN1 gene, and a fourth copy number of exon 8 of the SMN2 gene in the DNA sample from the product of the step (c); wherein when the sum of the first and the second copy numbers is not equal to the sum of the third and fourth copy numbers, then repeating steps (b) and (c) until the sum of the first and the second copy numbers equals to the sum of the third and fourth copy numbers; and (e) making a diagnosis of SMA based on the first copy number determined by the step (d).

In the step (a), a DNA sample is extracted from a cell or tissue of the human subject. The cell or tissue may be any available cell or tissue obtained from the human subject, as long as such the cell or tissue contains the DNA of the human subject. For example, the cell may be an epithelial cell, fibroblast, stem cell, blood cell, keratinocyte, or adipocyte. The tissue may be a tissue biopsy, such as a gastric, esophageal, colorectal, brain, hepatic, splenic, skin biopsy, amniotic fluid, chorionic villi, dried blood spot, or whole blood. According to one example of the present disclosure, the DNA sample was extracted from the blood sample of the human subject. The DNA sample may be extracted from the cell or tissue by a commercial kit, or any conventional DNA extraction technique; for example, the phenol/chloroform assay, and detergent (e.g., sodiumdodecyl sulfate, TWEEN®-20, NP-40, and TRITON® X-100)/acetic acid assay.

Then, the extracted DNA sample is mixed with the present PCR reagents containing the first to the eighth primers, followed by PCR amplification as respectively illustrated in the steps (b) and (c). According to some embodiments of the present disclosure, the final concentration of each of the first to the third primers in the PCR reagents is 0.85 nM, the final concentration of each of the fourth to the sixth primers in the PCR reagents is 1.2 µM, and the final concentration of each of the seventh and the eighth primers in the PCR reagents is 3.0 µM.

In the step (d), the copy numbers of the exon sequences (i.e., exons 7 and 8 of SMN1 gene, and exons 7 and 8 of SMN2 gene) in the PCR product of the step (c) are determined. Depending on desired purposes, the copy numbers of the exon sequences may be determined by a gene sequencing assay, an electrophoresis assay (e.g., agarose gel electrophoresis, or capillary electrophoresis assay), or an immunological assay. According to some embodiments of the present disclosure, the peak areas of the DNA fragments (e.g., the exon 7 and exon 8 fragments) amplified by the PCR process are first analyzed by a capillary electrophoresis assay, and then, normalized by the peak areas of the internal controls. In one specific embodiment, a normalized value (alternatively, the ratio of peak area, R) is first calculated from the peak area of the exon gene using the equation of, $$\text{Normalized value} = \frac{(\text{peak area of exon gene in } T)/(\text{sum of peak areas of } ACTB \text{ and } HBB \text{ genes in } T)}{(\text{peak area of exon gene in } RS)/(\text{sum of peak areas of } ACTB \text{ and } HBB \text{ genes in } RS)}$$

wherein T represents the testing sample derived from a subject (i.e., a subject suspected of having SMA or being a carrier of SMA), and RD represents the sample derived from a normal healthy control (i.e., a subject not having SMA nor being an SMA carrier). According to one working example of the present disclosure, the copy number of each exon sequence in the testing sample is obtained from the normalized value in accordance with the criteria set forth in Table 4 of the present disclosure. Alternatively, the copy number of each exon sequence in the testing sample can be determined from the normalized value via a calibration plot constructed by the DNA templates comprising specific copy numbers (e.g., 0, 1, 2, 3, 4, 5, and 6 copy numbers) of exon 7 of SMN1 gene, exon 8 of SMN1 gene, exon 7 of SMN2 gene and/or exon 8 of SMN2 gene. As would be appreciated, the method for determining the copy numbers of the exon sequences should not be limited thereto.

According to some embodiments of the present disclosure, the sum of the copy number of exon 7 of SMN1 gene and the copy number of exon 7 of SMN2 gene (i.e., the copy number of exon 7 in SMN1 gene+ the copy number of exon 7 in SMN2 gene) should be equal to the sum of the copy number of exon 8 of SMN1 gene and the copy number of exon 8 of SMN2 gene (i.e., the copy number of exon 8 in SMN1 gene+ the copy number of exon 8 in SMN2 gene). The sum of the copy numbers of exon 7 in SMN1 and SMN2 genes not equal to the sum of the copy numbers of exon 8 in SMN1 and SMN2 genes indicates that the PCR condition should be adjusted and/or there is an error occurred during the PCR process. In this case, the PCR condition should be confirmed and/or the PCR process should be re-conducted so as to fix the PCR error. According to one example, each copy number of exons 7 and 8 in SMN1 gene is 0, and each copy number of exons 7 and 8 in SMN2 gene is 2; in this example, the sum of the copy numbers of exon 7 in SMN1 and SMN2 genes is 2, and the sum of the copy numbers of exon 8 in SMN1 and SMN2 genes is also 2. According to another example, each copy number of exons 7 and 8 in SMN1 gene is 0, and each copy number of exons 7 and 8 in SMN2 gene is 3; in this example, the sum of the copy numbers of exon 7 in SMN1 and SMN2 genes is 3, and the sum of the copy numbers of exon 8 in SMN1 and SMN2 genes is also 3. According to another example, the copy numbers of exons 7 and 8 in SMN1 gene are respectively 0 and 2, and the copy numbers of exons 7 and 8 in SMN2 gene are respectively 3 and 1; in this example, the sum of the copy numbers of exon 7 in SMN1 and SMN2 genes is 3, and the sum of the copy numbers of exon 8 in SMN1 and SMN2 genes is also 3. According to still another example, the copy numbers of exons 7 and 8 in SMN1 gene are respectively 0 and 1, and the copy numbers of exons 7 and 8 in SMN2 gene are respectively 4 and 3; in this example, the sum of the copy numbers of exon 7 in SMN1 and SMN2 genes is 4, and the sum of the copy numbers of exon 8 in SMN1 and SMN2 genes is also 4. According to further another example, the copy numbers of exons 7 and 8 in SMN1 gene are respectively 2 and 3, and the copy numbers of exons 7 and 8 in SMN2 gene are respectively 2 and 1; in this example, the sum of the copy numbers of exon 7 in SMN1 and SMN2 genes is 4, and the sum of the copy numbers of exon 8 in SMN1 and SMN2 genes is also 4.

Finally, in the step (e), a clinical practitioner or a skilled artisan may make a diagnosis of SMA based on the copy numbers as determined in the step (e). According to some embodiments of the present disclosure, in the case when the copy number of exon 7 in SMN1 gene is 0, then the human subject is diagnosed as having SMA; alternatively, in the case when the copy number of exon 7 in SMN1 gene is 1, then diagnosing the human subject is the carrier of the SMA.

Further, a clinical practitioner or a skilled artisan may determine the severity of SMA from the copy number of exon 8 of SMN1 gene, and the copy numbers of exons 7 and 8 of SMN2 gene. According to some embodiment, each copy number of exon 8 in SMN1 gene and exons 7 and 8 in SMN2 gene are inversely proportional to the severity of SMA.

The present diagnostic kit and method are advantageous in at least the five following aspects:

(1) The first to the third primers are useful in amplifying exon 7 of SMN1 and SMN2 genes, and the fourth to the sixth primers are useful in amplifying exon 8 of SMN1 and SMN2 genes. After the analysis of a detection technique (e.g., a capillary electrophoresis assay), a skilled artisan may determine the exon copy numbers of the SMN1 and SMN2 genes via detecting the profiles of the peaks respectively formed by the exon 7 and exon 8 fragments thereby diagnosing whether a subject has SMA or is an SMA carrier.

(2) The exons 7 and 8 of SMN1 and SMN2 genes are amplified by two steps in the present method. Specifically, in the first step of gene amplification, the sequence of exon 7 of SMN1 gene is amplified by the first and second primers (e.g., SEQ ID NOs: 9 and 10, respectively serving as the forward and reverse primers), and the sequence of exon 7 of SMN2 gene is amplified by the first and third primers (e.g., SEQ ID NOs: 9 and 11, respectively serving as the forward and reverse primers). The thus-obtained exon 7 fragments have the first non-human sequence (e.g., SEQ ID NO: 7) at the 5'-end thereof, and have the second non-human sequence (e.g., SEQ ID NO: 8) at the 5'-end thereof. Regarding the sequences of exon 8 of SMN1 and SMN2 genes, they are respectively amplified by the fourth and fifth primers (e.g., SEQ ID NOs: 12 and 13, respectively serving as the forward and reverse primers of the sequence of exon 8 of SMN1 gene) and the fourth and sixth primers (e.g., SEQ ID NOs: 12 and 14, respectively serving as the forward and reverse primers of the sequence of exon 8 of SMN2 gene), and the thus-obtained exon 8 fragments have the second non-human sequence (e.g., SEQ ID NO: 8) at the 5'-end thereof, and have the first non-human sequence (e.g., SEQ ID NO: 7) at the 5'-end thereof. Then, in the second step of gene amplification, the exon 7 and exon 8 fragments may further be amplified by the seventh and eighth primers (e.g., SEQ ID NOs: 7 and 8) via binding to the first and second non-human sequences of the exon 7 and exon 8 fragments. The employments of the first and second non-human sequences in the first to the sixth primers ensure that desired polynucleotides (e.g., the sequences of exons 7 and 8 of SMN1 and SMN2 genes) can be efficiently amplified so that a skilled artisan may accurately quantify the copy numbers of the desired polynucleotides.

(3) One mispairing nucleotide is introduced in the 3'-end of the second and/or third primers (i.e., the reverse primers for amplifying the sequence of exon 7 of SMN1 and SMN2 gene) so that the amplified exon 7 fragment of SMN1 gene can be distinguished from the amplified exon 7 fragment of SMN2 genes, and the diagnostic specificity is improved. According to one exemplary embodiment, the second primer comprises the nucleotide sequence of "CGG" at its 3'-end, in which the first nucleotide "G" is mispaired with the corresponding nucleotide "A" of exon 7 of SMN1 gene; and the third primer comprises the nucleotide sequence of "ATA" at its 3'-end, in which the first nucleotide "A" is mispaired with the corresponding nucleotide "G" of exon 7 of SMN2 gene. Similarly, one mispairing nucleotide is introduced in the 3'-end of the fifth and/or sixth primers (i.e., the forward primers for amplifying the sequence of exon 8 of SMN1 and SMN2 gene) for the purpose of improving the diagnostic specificity.

(4) As described above, the sum of the copy numbers of exon 7 in SMN1 and SMN2 genes should be equal to the sum of the copy numbers of exon 8 in SMN1 and SMN2 genes. The sum of the copy numbers of exon 7 sequence not equal to the sum of the copy numbers of exon 8 sequence indicates that the PCR condition should be adjusted and/or there is an error occurred during the PCR process, and the PCR condition should be confirmed and/or the PCR process should be re-conducted to fix the PCR error. The built-in control design ensures the accuracy and precision of sequence quantification.

(5) Compared to conventional methodology, which takes a lot of time for the analytic process and requires large amount of DNA samples, 10-120 ng of DNA sample is sufficient to be analyzed by the present kit and method, and the analytic process may be accomplished in 3 hours.

(II-3) Methods for Treating SMA

Based on the diagnostic result as described in Section (II-2) of the present disclosure, a clinical practitioner or a skilled artisan may administer to an SMA patient a suitable treatment in time thereby relieving symptoms associated with SMA. Alternatively, in the case when the subject is diagnosed as an SMA carrier, then a genetic counseling and management options available are provided.

Accordingly, another aspect of the present disclosure pertains to a method of treating a human subject having SMA. The method comprises, (a) extracting a DNA sample from the human subject;

(b) mixing the DNA sample with the first to eighth primers in the PCR reagents;

(c) subjecting the mixture of the step (b) to PCR;

(d) determining a first copy number of exon 7 of survival of motor neuron 1 (SMN1) gene, a second copy number of exon 7 of survival of motor neuron 2 (SMN2) gene, a third copy number of exon 8 of the SMN1 gene, and a fourth copy number of exon 8 of the SMN2 gene in the DNA sample from the product of the step (c); wherein when the sum of the first and the second copy numbers is not equal to the sum of the third and fourth copy numbers, then repeating steps (b) and (c) until the sum of the first and the second copy numbers equals to the sum of the third and fourth copy numbers; and (e) treating the SMA based on the first copy number determined by the step (d), wherein when the first copy number is 0, administering to the human subject an effective amount of a therapeutic agent.

The steps (a) to (d) of the therapeutic method are quite similar to those aforementioned, and hence, detailed description thereof is omitted herein for the sake of brevity.

In the step (e), a therapeutic agent is administered to the human subject having SMA so as to alleviate or ameliorate the symptoms associated with SMA. Examples of the therapeutic agent include, but are not limited to, nusinersen (Spinraza®), risdiplam (Evrysdi™), onasemnogene abeparvovec (Zolgensma®) or a combination thereof. Additionally or alternatively, the human subject may receive an SMA gene therapy or any other treatment that provides a beneficial effect on SMA, e.g., an intervention therapy. Further, a clinical practitioner or a skilled artisan may determine the dosage regimen of the therapeutic agent administered to the subject (e.g., the frequency of administration, the dose per administration, the time interval between administrations, and duration of treatments) in accordance with the copy numbers of exon 8 of SMN1 gene and exons 7 and 8 of SMN2 that as aforementioned inversely proportional to the severity of SMA.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

PCR Primers

Eight PCR primers were synthesized in the present study to detect the copy number of exons 7 and 8 of SMN1 and SMN2 genes. The polynucleotide sequences of the present primers were respectively listed in Table 1.

TABLE 1

The polynucleotide sequences of the present PCR primers

| Name | Polynucleotide sequence (from the 5'-end to the 3'end)* | SEQ ID NO |
|---|---|---|
| P1 | TCGACGCACGCTCCTGCTACAGCAGCCTAATAATTGTTTTCTTTGGG | 9 |
| P2 | TGACCGTCTGCGCCTCGTTCCCTTCCTTCTTTTTGATTTTGTCGG | 10 |
| P3 | TGACCGTCTGCGCCTCGTTCACTTCACCTTCCTTCTTTTTGATTTTGTATA | 11 |
| P4 | TCGACGCACGCTCCTGCTACAAGCCATGTCCACCAGTTAGATTC | 12 |
| P5 | TGACCGTCTGCGCCTCGTTCAAACCATCTGTAAAAGACCGG | 13 |
| P6 | TGACCGTCTGCGCCTCGTTCACTTCAAACCATCTGTAAAAGACGGA | 14 |

TABLE 1-continued

The polynucleotide sequences of the present PCR primers

| Name | Polynucleotide sequence (from the 5'-end to the 3' end)* | SEQ ID NO |
|---|---|---|
| P7 | TCGACGCACGCTCCTGCTACA | 7 |
| P8 | TGACCGTCTGCGCCTCGTTC | 8 |

*The first non-human sequence is marked by underlining; the second non-human sequence is marked by double underlining; and the third non-human sequence is marked in boldface.

PCR Assay

The PCR solution (18 µl) comprising the primers of Table 2 were mixed with DNA polymerase (0.16 µl) and DNA sample (2 µl), followed by amplifying the DNA molecules of the DNA sample via a PCR process. The PCR condition was summarized in Table 3.

TABLE 2

The concentration of specified components of PCR solutions

| Name | PCR solution Final concentration | | | |
|---|---|---|---|---|
| 10× PCR buffer | 1× | | | |
| 25 mM MgCl₂ | 0.5 mM | | | |
| dATP | 0.25 mM | | | |
| dTTP | 0.25 mM | | | |
| dGTP | 0.25 mM | | | |
| dCTP | 0.25 mM | | | |
| Betaine | 1.85M | | | |
| 1× TE buffer | 1× | | | |
| PCR primers | P1: 0.85 µM | P5: 1.2 µM | ACTB_F: 0.5 µM | |
| | P2: 0.85 µM | P6: 1.2 µM | ACTB_R: 0.5 µM | |
| | P3: 0.85 µM | P7: 3.0 µM | HBB_F: 0.45 µM | |
| | P4: 1.2 µM | P8: 3.0 µM | HBB_R: 0.45 µM | |

(1) Final volume of each PCR solution: 18 µl.
(2) Total reaction volume: 20.16 µl, including 18 µl PCR solution, 0.16 µl DNA polymerase, and 2 µl DNA sample.
(3) ACTB_F: the forward primer of beta-actin gene, SEQ ID NO: 15; ACTB_R: the reverse primer of beta-actin gene, SEQ ID NO: 16; HBB_F: the forward primer of haemoglobin beta gene, SEQ ID NO: 17; HBB_R: the reverse primer of haemoglobin beta gene, SEQ ID NO: 18. The beta-actin (ACTB) gene and the haemoglobin beta (HBB) gene served as internal controls of the present invention.

TABLE 3

PCR condition for amplifying DNA fragments PCR conditions

| | |
|---|---|
| | 95° C./5 minutes |
| 25 cycles | 95° C./30 seconds |
| | 57° C./30 seconds |
| | 72° C./30 seconds |
| | 72° C./30 minutes |
| | 4° C./overnight |

After the PCR process, 0.5 µl PCR product was mixed with 0.5 µl LIZ size standard and 9 µl deionized formamide, and analyzed by capillary electrophoresis. Four peak areas, respectively corresponding to the PCR products of exon 7 of SMN1 gene, exon 8 of SMN1 gene, exon 7 of SMN2 gene and exon 8 of SMN2 gene, were obtained from the electrophoresis followed by normalizing with the peak areas of house-keeping genes (i.e., the PCR products amplified by ACTB_F, ACTB_R, HBB_F and HBB_R) and the peak areas of normal control. The sum of the copy numbers of exon 7 of SMN1 and SMN2 genes should be equal to the sum of the copy numbers of exon 8 of SMN1 and SMN2 genes. In the case when the sum of the copy numbers of exon 7 sequence in SMN1 and SMN2 genes was not equal to the sum of the copy numbers of exon 8 sequence in SMN1 and SMN2 genes, the PCR condition was confirmed and the PCR process was re-conducted so as to fix the error occurred during the PCR process.

Specifically, a normalized value (alternatively, the ratio of peak area, R) was first calculated from the peak area of each exon gene using the equation of, $$\text{Normalized value} = \frac{(\text{peak area of exon gene in } T)/(\text{sum of peak areas of } ACTB \text{ and } HBB \text{ genes in } T)}{(\text{peak area of exon gene in } RS)/(\text{sum of peak areas of } ACTB \text{ and } HBB \text{ genes in } RS)}$$

wherein T represents the testing sample derived from a subject (i.e., a subject suspected of having SMA or being a carrier of SMA), and RD represents the sample derived from a normal healthy control (i.e., a subject not having SMA nor being an SMA carrier).

The copy number of each exon sequence in the testing sample was then obtained from the normalized value in accordance with the criteria set forth in Table 4.

TABLE 4

Criteria for evaluating the copy numbers of exon sequences

| Copy number | Normalized value (R) |
|---|---|
| 0 | R ≤ 0.37 |
| 1 | 0.37 ≤ R < 1.41 |
| 2 | 1.41 ≤ R < 2.45 |
| 3 | 2.45 ≤ R < 3.5 |
| ≥4 | R ≥ 3.50 |

Whether the subject has SMA or is an SMA carrier was determined based on the copy number of exon 7 of SMN1 gene. For example, when the copy number was equal to or greater than 2 (i.e., 2, 3, 4, 5 or 6), the subject was determined to be a healthy subject (i.e., a subject not having SMA nor being an SMA carrier). In the case when the copy number was 1, then the subject was determined to be an SMA carrier. Alternatively, when the copy number was 0, then the subject was determined to be an SMA patient. The severity of SMA may further be determined from the copy numbers of exon 8 of SMN1 gene and exons 7 and 8 of SMN2, which were inversely proportional to the severity of SMA.

Preparation of Normal Control

The vectors respectively containing 2 copies of exon 7 of SMN1 gene, 2 copies of exon 8 of SMN1 gene, 2 copies of exon 7 of SMN2 gene, and 2 copies of exon 8 of SMN2 gene were mixed at a ratio of 1:1:1:1. The final concentration was 14,500 copies/µ.

Preparation of Mutation Samples

Four mutation samples, including PC01 to PC04, were included in the present invention. The components of the mutation samples were summarized in Table 5. The samples were diluted by ddH$_2$O to a working concentration of 5, 25 or 60 ng/μl.

TABLE 5

Components of mutation samples

| Name | Copy number of SMN1 exon 7 | Copy number of SMN2 exon 7 | Copy number of SMN1 exon 8 | Copy number of SMN2 exon 8 |
|---|---|---|---|---|
| PC01 | 0 | 1 | 0 | 1 |
| PC02 | 0 | 2 | 0 | 2 |
| PC03 | 0 | 3 | 0 | 3 |
| PC04 | 0 | 4 | 0 | 4 |

Preparation of Carrier Samples

Five carrier samples, including PC05 to PC09, were included in the present invention. The components of the mutation samples were summarized in Table 6. The samples were diluted by ddH$_2$O to a working concentration of 5, 25 or 60 ng/μl.

TABLE 6

Components of carrier samples

| Name | Copy number of SMN1 exon 7 | Copy number of SMN2 exon 7 | Copy number of SMN1 exon 8 | Copy number of SMN2 exon 8 |
|---|---|---|---|---|
| PC05 | 1 | 0 | 1 | 0 |
| PC06 | 1 | 1 | 1 | 1 |
| PC07 | 1 | 2 | 1 | 2 |
| PC08 | 1 | 3 | 1 | 3 |
| PC09 | 1 | 4 | 1 | 4 |

Preparation of Normal Samples

Twelve normal samples, including NC01 to NC12, were included in the present invention. The components of the mutation samples were summarized in Table 7. The samples were diluted by ddH$_2$O to a working concentration of 5, 25 or 60 ng/μl.

TABLE 7

Components of normal samples

| Name | Copy number of SMN1 exon 7 | Copy number of SMN2 exon 7 | Copy number of SMN1 exon 8 | Copy number of SMN2 exon 8 |
|---|---|---|---|---|
| NC01 | 2 | 0 | 2 | 0 |
| NC02 | 2 | 1 | 2 | 1 |
| NC03 | 2 | 2 | 2 | 2 |
| NC04 | 2 | 3 | 2 | 3 |
| NC05 | 2 | 4 | 2 | 4 |
| NC06 | 3 | 0 | 3 | 0 |
| NC07 | 3 | 1 | 3 | 1 |
| NC08 | 3 | 2 | 3 | 2 |
| NC09 | 3 | 3 | 3 | 3 |
| NC10 | 4 | 0 | 4 | 0 |
| NC11 | 4 | 1 | 4 | 1 |
| NC12 | 4 | 2 | 4 | 2 |

Preparation of Repetitive Samples

Three repetitive samples, including LPC01, LPC02 and LNC01, were included in the present invention. The components of the mutation samples were summarized in Table 8. The samples were diluted by ddH$_2$O to a working concentration of 5 or 25 ng/μl.

TABLE 8

Components of repetitive samples

| Name | Copy number of SMN1 exon 7 | Copy number of SMN2 exon 7 | Copy number of SMN1 exon 8 | Copy number of SMN2 exon 8 |
|---|---|---|---|---|
| LPC01 | 1 | 0 | 1 | 0 |
| LPC02 | 0 | 1 | 0 | 1 |
| LNC01 | 2 | 2 | 2 | 2 |

Preparation of Minimum Samples

Tweeny one minimum samples, including LOD01 to LOD21, were included in the present invention. The components of the mutation samples were summarized in Table 9. The samples were diluted by ddH2O to a working concentration of 5, 10 or 15 ng/μl.

TABLE 9

Components of repetitive samples

| Name | Copy number of SMN1 exon 7 | Copy number of SMN2 exon 7 | Copy number of SMN2 exon 8 | Copy number of SMN2 exon 8 |
|---|---|---|---|---|
| LOD01 | 0 | 1 | 0 | 1 |
| LOD02 | 0 | 2 | 0 | 2 |
| LOD03 | 0 | 3 | 0 | 3 |
| LOD04 | 0 | 4 | 0 | 4 |
| LOD05 | 1 | 0 | 1 | 0 |
| LOD06 | 1 | 1 | 1 | 1 |
| LOD07 | 1 | 2 | 1 | 2 |
| LOD08 | 1 | 3 | 1 | 3 |
| LOD09 | 1 | 4 | 1 | 4 |
| LOD10 | 2 | 0 | 2 | 0 |
| LOD11 | 2 | 1 | 2 | 1 |
| LOD12 | 2 | 2 | 2 | 2 |
| LOD13 | 2 | 3 | 2 | 3 |
| LOD14 | 2 | 4 | 2 | 4 |
| LOD15 | 3 | 0 | 3 | 0 |
| LOD19 | 3 | 1 | 3 | 1 |
| LOD17 | 3 | 2 | 3 | 2 |
| LOD18 | 3 | 3 | 3 | 3 |
| LOD19 | 4 | 0 | 4 | 0 |
| LOD20 | 4 | 1 | 4 | 1 |
| LOD21 | 4 | 2 | 4 | 2 |

Example 1 Evaluation of the Diagnostic Accuracy of the Present Kit

Figure 2:
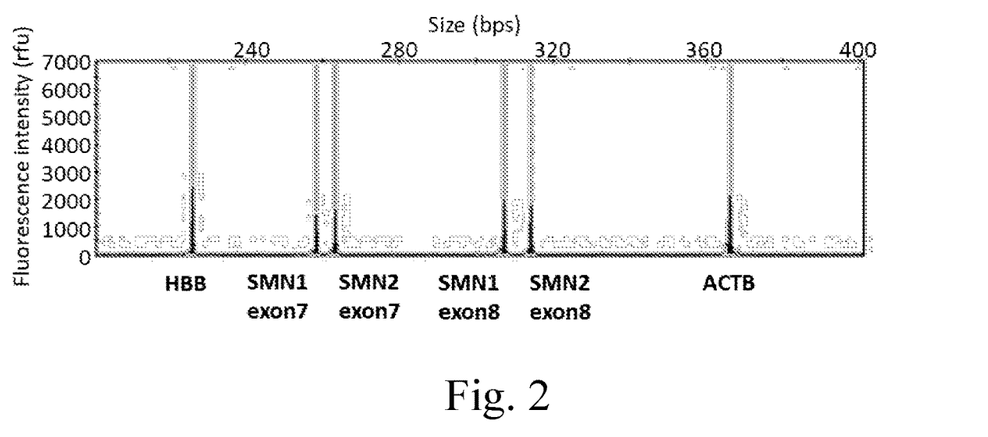
FIG. 2 is an electropherogram depicting the analytic result of normal control according to Example 1 of the present disclosure, in which the normal control contained four vectors respectively carrying 2 copies of exon 7 of SMN1 gene, 2 copies of exon 8 of SMN1 gene, 2 copies of exon 7 of SMN2 gene, and 2 copies of exon 8 of SMN2 gene. The analytic result indicated that the ratio of the copy number of SMN1 gene to the copy number of SMN2 gene in the normal control was 2:2.

For the purpose of evaluating the accuracy of the present kit, the normal control (i.e., four vectors respectively carried specific copy number of exon sequence), the mutation samples (i.e., PC01 to PC04), carrier samples (i.e., PC05 to PC09) and normal samples (i.e., NC01 to NC12) were respectively mixed with the present kit followed by the analysis of capillary electrophoresis. Each experiment was repeated for three times. According to analytic results, the present kit was capable of identifying the samples containing different copy numbers of SMN1 exon 7, SMN1 exon 8, SMN2 exon 7 and SMN2 exon 8 (FIG. 2), and the accuracy of the present kit on determining the copy numbers in the testing samples was 100% (data not shown).

Further, the present kit was mixed with the repetitive samples (i.e., LPC01, LPC02 and LNC01) and minimum samples (i.e., LOD01 to LOD21) followed by the analysis of capillary electrophoresis. The experiments were respectively repeated for ten and twenty times. The data indicated that the present kit was capable of accurately determining the copy numbers of SMN1 exon 7, SMN1 exon 8, SMN2 exon 7 and SMN2 exon 8 (data not shown).

Example 2 Determination of Exon Copy Number in Human Subjects

The whole blood samples were isolated from 143 human subjects, including 15 SMA patients, 20 SMA carriers, and 108 normal subjects. The DNA samples extracted therefrom were mixed with the present primers, and then processed in accordance with the procedure mentioned in Materials and Methods of the present disclosure. The data was summarized in Table 10.

TABLE 10

Determination of exon copy number in human subjects by the present kit

| Sample | Subject | MLPA* | CN** of exon 7 of SMN1: CN of exon 7 of SMN2/CN of exon 8 of SMN1: CN of exon 8 of SMN2 The present kit |
|---|---|---|---|
| 1 | SMA patient | 0:2/0:2 | 0:2/0:2 |
| 2 | SMA patient | 0:2/0:2 | 0:2/0:2 |
| 3 | SMA patient | 0:2/0:2 | 0:2/0:2 |
| 4 | SMA patient | 0:3/0:3 | 0:3/0:3 |
| 5 | SMA patient | 0:3/0:3 | 0:3/0:3 |
| 6 | SMA patient | 0:3/0:3 | 0:3/0:3 |
| 7 | SMA patient | 0:3/0:3 | 0:3/0:3 |
| 8 | SMA patient | 0:4/0:4 | 0:≥4/0:≥4 |
| 9 | SMA patient | 0:3/0:3 | 0:3/0:3 |
| 10 | SMA patient | 0:3/0:3 | 0:3/0:3 |
| 11 | SMA patient | 0:3/0:3 | 0:3/0:3 |
| 12 | SMA patient | 0:3/2:1 | 0:3/2:1 |
| 13 | SMA patient | 0:3/1:2 | 0:3/1:2 |
| 14 | SMA patient | 0:4/1:3 | 0:≥4/1:3 |
| 15 | SMA patient | 0:2/1:1 | 0:2/1:1 |
| 16 | SMA carrier | 1:0/1:0 | 1:0/1:0 |
| 17 | SMA carrier | 1:1/1:1 | 1:1/1:1 |
| 18 | SMA carrier | 1:1/1:1 | 1:1/1:1 |
| 19 | SMA carrier | 1:1/1:1 | 1:1/1:1 |
| 20 | SMA carrier | 1:1/1:1 | 1:1/1:1 |
| 21 | SMA carrier | 1:2/1:2 | 1:2/1:2 |
| 22 | SMA carrier | 1:2/1:2 | 1:2/1:2 |
| 23 | SMA carrier | 1:2/1:2 | 1:2/1:2 |
| 24 | SMA carrier | 1:2/1:2 | 1:2/1:2 |
| 25 | SMA carrier | 1:2/1:2 | 1:2/1:2 |
| 26 | SMA carrier | 1:2/1:2 | 1:2/1:2 |
| 27 | SMA carrier | 1:2/1:2 | 1:2/1:2 |
| 28 | SMA carrier | 1:2/1:2 | 1:2/1:2 |
| 29 | SMA carrier | 1:3/1:3 | 1:3/1:3 |
| 30 | SMA carrier | 1:3/1:3 | 1:3/1:3 |
| 31 | SMA carrier | 1:4/1:4 | 1:≥4/1:≥4 |
| 32 | SMA carrier | 1:4/1:4 | 1:≥4/1:≥4 |
| 33 | SMA carrier | 1:1/2:0 | 1:1/2:0 |
| 34 | SMA carrier | 1:3/0:4 | 1:3/0:≥4 |
| 35 | SMA carrier | 1:1/0:2 | 1:1/0:2 |
| 36 | normal subject | 2:0/2:0 | 2:0/2:0 |
| 37 | normal subject | 2:0/2:0 | 2:0/2:0 |
| 38 | normal subject | 2:0/2:0 | 2:0/2:0 |
| 39 | normal subject | 2:0/2:0 | 2:0/2:0 |
| 40 | normal subject | 2:0/2:0 | 2:0/2:0 |
| 41 | normal subject | 2:0/2:0 | 2:0/2:0 |
| 42 | normal subject | 2:0/2:0 | 2:0/2:0 |
| 43 | normal subject | 2:1/2:1 | 2:1/2:1 |
| 44 | normal subject | 2:1/2:1 | 2:1/2:1 |
| 45 | normal subject | 2:1/2:1 | 2:1/2:1 |
| 46 | normal subject | 2:1/2:1 | 2:1/2:1 |
| 47 | normal subject | 2:1/2:1 | 2:1/2:1 |
| 48 | normal subject | 2:2/2:2 | 2:2/2:2 |
| 49 | normal subject | 2:2/2:2 | 2:2/2:2 |
| 50 | normal subject | 2:2/2:2 | 2:2/2:2 |
| 51 | normal subject | 2:2/2:2 | 2:2/2:2 |
| 52 | normal subject | 2:2/2:2 | 2:2/2:2 |
| 53 | normal subject | 2:2/2:2 | 2:2/2:2 |
| 54 | normal subject | 2:2/2:2 | 2:2/2:2 |
| 55 | normal subject | 2:2/2:2 | 2:2/2:2 |
| 56 | normal subject | 2:2/2:2 | 2:2/2:2 |
| 57 | normal subject | 2:2/2:2 | 2:2/2:2 |
| 58 | normal subject | 2:2/2:2 | 2:2/2:2 |
| 59 | normal subject | 2:2/2:2 | 2:2/2:2 |
| 60 | normal subject | 2:3/2:3 | 2:3/2:3 |
| 61 | normal subject | 2:3/2:3 | 2:3/2:3 |
| 62 | normal subject | 2:3/2:3 | 2:3/2:3 |
| 63 | normal subject | 2:3/2:3 | 2:3/2:3 |
| 64 | normal subject | 2:3/2:3 | 2:3/2:3 |
| 65 | normal subject | 2:3/2:3 | 2:3/2:3 |
| 66 | normal subject | 2:4/2:4 | 2:≥4/2:≥4 |
| 67 | normal subject | 2:4/2:4 | 2:≥4/2:≥4 |
| 68 | normal subject | 2:4/2:4 | 2:≥4/2:≥4 |
| 69 | normal subject | 2:4/2:4 | 2:≥4/2:≥4 |
| 70 | normal subject | 2:5/2:5 | 2:≥4/2:≥4 |
| 71 | normal subject | 3:0/3:0 | 3:0/3:0 |
| 72 | normal subject | 3:0/3:0 | 3:0/3:0 |
| 73 | normal subject | 3:0/3:0 | 3:0/3:0 |
| 74 | normal subject | 3:0/3:0 | 3:0/3:0 |
| 75 | normal subject | 3:0/3:0 | 3:0/3:0 |
| 76 | normal subject | 3:0/3:0 | 3:0/3:0 |
| 77 | normal subject | 3:1/3:1 | 3:1/3:1 |
| 78 | normal subject | 3:1/3:1 | 3:1/3:1 |
| 79 | normal subject | 3:1/3:1 | 3:1/3:1 |
| 80 | normal subject | 3:1/3:1 | 3:1/3:1 |
| 81 | normal subject | 3:1/3:1 | 3:1/3:1 |
| 82 | normal subject | 3:1/3:1 | 3:1/3:1 |
| 83 | normal subject | 3:1/3:1 | 3:1/3:1 |
| 84 | normal subject | 3:2/3:2 | 3:2/3:2 |
| 85 | normal subject | 3:2/3:2 | 3:2/3:2 |
| 86 | normal subject | 3:2/3:2 | 3:2/3:2 |
| 87 | normal subject | 3:2/3:2 | 3:2/3:2 |
| 88 | normal subject | 3:2/3:2 | 3:2/3:2 |
| 89 | normal subject | 3:2/3:2 | 3:2/3:2 |
| 90 | normal subject | 3:2/3:2 | 3:2/3:2 |
| 91 | normal subject | 3:3/3:3 | 3:3/3:3 |
| 92 | normal subject | 3:3/3:3 | 3:3/3:3 |
| 93 | normal subject | 3:3/3:3 | 3:3/3:3 |
| 94 | normal subject | 3:3/3:3 | 3:3/3:3 |
| 95 | normal subject | 3:4/3:4 | 3:≥4/3:≥4 |
| 96 | normal subject | 3:5/3:5 | 3:≥4/3:≥4 |
| 97 | normal subject | 4:0/4:0 | ≥4:0/≥4:0 |
| 98 | normal subject | 4:0/4:0 | ≥4:0/≥4:0 |
| 99 | normal subject | 4:1/4:1 | ≥4:1/≥4:1 |
| 100 | normal subject | 4:1/4:1 | ≥4:1/≥4:1 |
| 101 | normal subject | 4:1/4:1 | ≥4:1/≥4:1 |
| 102 | normal subject | 4:2/4:2 | ≥4:2/≥4:2 |
| 103 | normal subject | 4:2/4:2 | ≥4:2/≥4:2 |
| 104 | normal subject | 4:2/4:2 | ≥4:2/≥4:2 |
| 105 | normal subject | 4:2/4:2 | ≥4:2/≥4:2 |
| 106 | normal subject | 4:2/4:2 | ≥4:2/≥4:2 |
| 107 | normal subject | 4:2/4:2 | ≥4:2/≥4:2 |
| 108 | normal subject | 4:3/4:3 | ≥4:3/≥4:3 |
| 109 | normal subject | 4:4/4:4 | ≥4:≥4/≥4:≥4 |
| 110 | normal subject | 4:4/4:4 | ≥4:≥4/≥4:≥4 |
| 111 | normal subject | 4:4/4:4 | ≥4:≥4/≥4:≥4 |
| 112 | normal subject | 4:4/4:4 | ≥4:≥4/≥4:≥4 |
| 113 | normal subject | 5:1/5:1 | ≥4:1/≥4:1 |
| 114 | normal subject | 5:1/5:1 | ≥4:1/≥4:1 |
| 115 | normal subject | 5:1/5:1 | ≥4:1/≥4:1 |
| 116 | normal subject | 5:1/5:1 | ≥4:1/≥4:1 |
| 117 | normal subject | 5:2/5:2 | ≥4:2/≥4:2 |
| 118 | normal subject | 5:2/5:2 | ≥4:2/≥4:2 |
| 119 | normal subject | 5:3/5:3 | ≥4:3/≥4:3 |
| 120 | normal subject | 5:3/5:3 | ≥4:3/≥4:3 |
| 121 | normal subject | 6:1/6:1 | ≥4:1/≥4:1 |
| 122 | normal subject | 2:3/3:2 | 2:3/3:2 |
| 123 | normal subject | 2:3/3:2 | 2:3/3:2 |
| 124 | normal subject | 2:3/3:2 | 2:3/3:2 |
| 125 | normal subject | 1:3/3:1 | 1:3/3:1 |

TABLE 10-continued

Determination of exon copy number in human subjects by the present kit

| Sample | Subject | MLPA* | The present kit |
|---|---|---|---|
| | | CN** of exon 7 of SMN1: CN of exon 7 of SMN2/CN of exon 8 of SMN1: CN of exon 8 of SMN2 | |
| 126 | normal subject | 2:2/1:3 | 2:2/1:3 |
| 127 | normal subject | 2:2/1:3 | 2:2/1:3 |
| 128 | normal subject | 2:2/1:3 | 2:2/1:3 |
| 129 | normal subject | 2:3/1:4 | 2:3/1:≥4 |
| 130 | normal subject | 3:2/2:3 | 3:2/2:3 |
| 131 | normal subject | 3:1/2:2 | 3:1/2:2 |
| 132 | normal subject | 3:2/4:1 | 3:2/≥4:1 |
| 134 | normal subject | 3:3/4:2 | 3:3/≥4:2 |
| 135 | normal subject | 2:1/1:2 | 2:1/1:2 |
| 136 | normal subject | 2:2/4:0 | 2:2/≥4:0 |
| 137 | normal subject | 2:1/3:0 | 2:1/3:0 |
| 138 | normal subject | 2:1/1:2 | 2:1/1:2 |
| 139 | normal subject | 2:2/3:1 | 2:2/3:1 |
| 140 | normal subject | 2:3/4:1 | 2:3/≥4:1 |
| 141 | normal subject | 4:1/3:2 | ≥4:1/3:2 |
| 143 | normal subject | 5:5/4:6 | ≥4:≥4/≥4:≥4 |

*MLPA: Multiplex Ligation-dependent Probe Amplification, serving as positive control in the present invention.
**CN: copy number.

Figure 3:
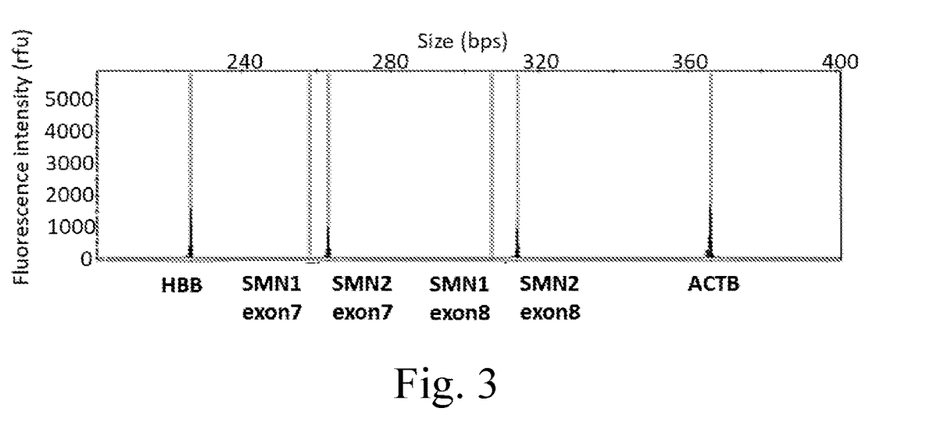
FIG. 3 is an electropherogram depicting the analytic result of DNA sample isolated from an SMA patient according to Example 2 of the present disclosure. The analytic result indicated that the ratio of the copy number of SMN1 gene to the copy number of SMN2 gene in the DNA sample of the SMA patient was 0:2.
Figure 4:
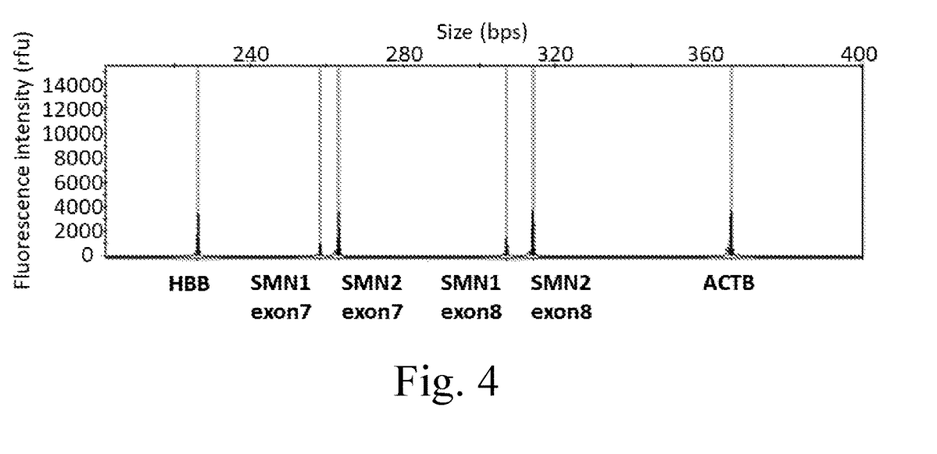
FIG. 4 is an electropherogram depicting the analytic result of DNA sample isolated from an SMA carrier according to Example 2 of the present disclosure. The analytic result indicated that the ratio of the copy number of SMN1 gene to the copy number of SMN2 gene in the DNA sample of the SMA carrier was 1:3.
Figure 5:
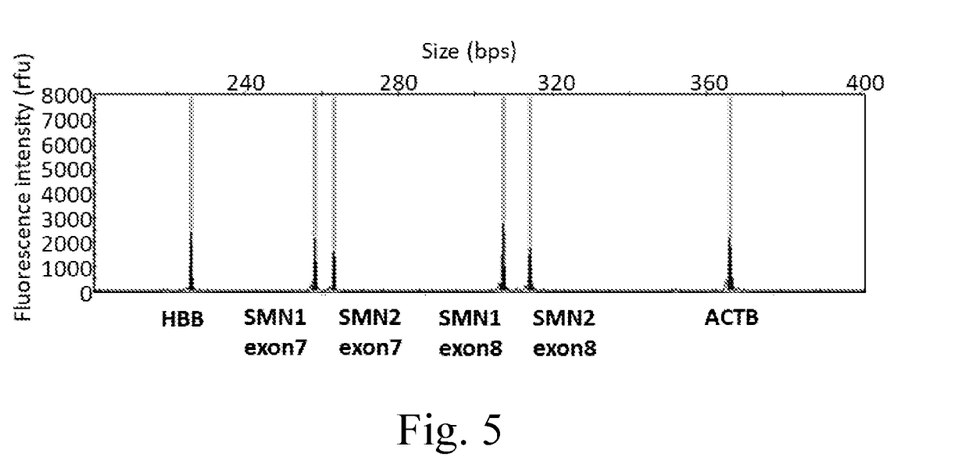
FIG. 5 is an electropherogram depicting the analytic result of DNA sample isolated from a normal subject according to Example 2 of the present disclosure. The analytic result indicated that the ratio of the copy number of SMN1 gene to the copy number of SMN2 gene in the DNA sample of the normal subject was 3:2.

According to the data of Table 10 and FIGS. 3-5, the present kit may accurately determine the exon copy numbers of human subjects thereby identifying the SMA patients, SMA carriers and normal subjects.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A kit for making a diagnosis as to whether a human subject has spinal muscular atrophy (SMA) or is a carrier of SMA, comprising,
   a first primer consisting of the polynucleotide sequence of SEQ ID NO: 9;
   a second primer consisting of the polynucleotide sequence of SEQ ID NO: 10;
   a third primer consisting of the polynucleotide sequence of SEQ ID NO: 11;
   a fourth primer consisting of the polynucleotide sequence of SEQ ID NO: 12;
   a fifth primer consisting of the polynucleotide sequence of SEQ ID NO: 13;
   a sixth primer consisting of the polynucleotide sequence of SEQ ID NO: 14;
   a seventh primer consisting of the polynucleotide sequence of SEQ ID NO: 7;
   an eighth primer consisting of the polynucleotide sequence of SEQ ID NO: 8; and
   polymerase chain reaction (PCR) reagents.

2. The kit of claim 1, further comprising two DNA templates, wherein
   the first DNA template has two copies of beta-actin gene within the polynucleotide sequence thereof; and
   the second DNA template has two copies of haemoglobin beta gene within the polynucleotide sequence thereof.

3. The kit of claim 1, wherein the PCR reagents comprise DNA polymerase, buffer, $MgCl_2$, deoxypolynucleotide triphosphates (dNTPs), and betaine.

4. A method of making a diagnosis as to whether a human subject has spinal muscular atrophy (SMA) or is a carrier of SMA by using the kit of claim 1, comprising,
   (a) extracting a DNA sample from the human subject;
   (b) mixing the DNA sample with the first to eighth primers in the PCR reagents;
   (c) subjecting the mixture of the step (b) to PCR;
   (d) determining a first copy number of exon 7 of survival of motor neuron 1 (SMN1) gene, a second copy number of exon 7 of survival of motor neuron 2 (SMN2) gene, a third copy number of exon 8 of the SMN1 gene, and a fourth copy number of exon 8 of the SMN2 gene in the DNA sample from the product of the step (c); wherein when the sum of the first and the second copy numbers is not equal to the sum of the third and fourth copy numbers, then repeating steps (b) and (c) until the sum of the first and the second copy numbers equals to the sum of the third and fourth copy numbers; and
   (e) making the diagnosis of SMA based on the first copy number determined by the step (d), wherein
      when the first copy number is 0, then diagnosing the human subject as having SMA; or
      when the first copy number is 1, then diagnosing the human subject as being a carrier of SMA.

* * * * *